United States Patent
Yuan et al.

(10) Patent No.: US 10,774,350 B2
(45) Date of Patent: Sep. 15, 2020

(54) METHOD FOR FERMENTATIVE PRODUCTION OF OXIDIZED COENZYME Q10

(71) Applicants: ZHEJIANG NHU COMPANY LTD., Hangzhou, Zhejiang Province (CN); ZHEJIANG UNIVERSITY, Hangzhou, Zhejiang Province (CN); HEILONGJIANG NHU BIOTECHNOLOGY COMPANY LTD., Sui Hua, Hei Longjiang Province (CN); SHANGYU NHU BIOLOGICAL CHEMICAL CO., LTD., Shaoxing, Zhejiang Province (CN)

(72) Inventors: Shenfeng Yuan, Hangzhou (CN); Hongwei Yu, Hangzhou (CN); Zhaofeng Chen, Shaoxing (CN); Yongqiang Zhu, Shaoxing (CN); Yi Min, Shaoxing (CN); Yong Li, Shaoxing (CN); Baishan Hu, Shaoxing (CN); Guisheng Qiu, Shaoxing (CN); Kai Yu, Shaoxing (CN)

(73) Assignees: ZHEJIANG NHU COMPANY LTD., Shaoxing (CN); ZHEJIANG UNIVERSITY, Hangzhou (CN); HEILONGJIANG NHU BIOTECHNOLOGY COMPANY LTD., Sui Hua (CN); SHANGYU NHU BIOLOGICAL CHEMICAL CO., LTD., Shaoxing (CN)

( * ) Notice: Subject to any disclaimer, the term of this patent is extended or adjusted under 35 U.S.C. 154(b) by 0 days.

(21) Appl. No.: 16/016,813

(22) Filed: Jun. 25, 2018

(65) Prior Publication Data
US 2019/0194704 A1     Jun. 27, 2019

Related U.S. Application Data

(63) Continuation of application No. PCT/CN2018/074822, filed on Jan. 31, 2018.

(30) Foreign Application Priority Data

Dec. 25, 2017   (CN) .......................... 2017 1 1421000

(51) Int. Cl.
C12P 7/66      (2006.01)
(52) U.S. Cl.
CPC ....................... C12P 7/66 (2013.01)
(58) Field of Classification Search
None
See application file for complete search history.

(56) References Cited

U.S. PATENT DOCUMENTS

| 7,910,340 B2 | 3/2011 | Yajima et al. | |
|---|---|---|---|
| 2005/0181490 A1* | 8/2005 | Cheong | C12N 9/1022 435/133 |
| 2006/0115884 A1* | 6/2006 | Burmaster | C12P 7/06 435/161 |

FOREIGN PATENT DOCUMENTS

| CN | 101705258 | | 5/2010 |
|---|---|---|---|
| CN | 102876743 A | | 1/2013 |
| CN | 102965272 A | | 3/2013 |
| CN | 103509728 | * | 1/2014 |
| CN | 103509729 | * | 1/2014 |
| CN | 103509729 A | | 1/2014 |
| CN | 104561154 A | | 4/2015 |
| CN | 105420417 A | | 3/2016 |
| CN | 105483171 A | | 4/2016 |
| CN | 105441371 | * | 6/2016 |
| WO | 2008-100782 A2 | | 8/2008 |
| WO | 2017-071529 A1 | | 5/2017 |

OTHER PUBLICATIONS

"Agitation-Aeration Studies on Coenzyme Q10 Production Using Rhodopseudomonas spheroides", Kuniaki Sakato, et al., Biotechnology and Applied Biochemistry 16, 19-28 (1992).
"Application of Fuzzy Control System to Coenzyme Q10 Fermentation", Yoshinobu Yamada, et al., Journal of Chemical Engineering of Japan, vol. 24, No. 1, 94-99 (1991).

* cited by examiner

Primary Examiner — Christian L Fronda
(74) Attorney, Agent, or Firm — Fish & Richardson P.C.

(57) ABSTRACT

The present application relates to a method for fermentative production of oxidized coenzyme Q10 and high-content oxidized coenzyme Q10 prepared therefrom. For the method for fermentative production of oxidized coenzyme Q10, in a fermentation process of a production strain, the oxidation-reduction potential (ORP) of a fermentation broth is controlled to be −50 to 300 Mv, and preferably the oxidation-reduction potential (ORP) of the fermentation broth is controlled to be 50 to 200 mV. By controlling the ORP of the fermentation broth, the method for fermentative production of oxidized coenzyme Q10 enables the oxidized coenzyme Q10 content in the coenzyme Q10 produced by microorganisms to reach 96% or more, and the product is substantially composed of a single component, which makes post-treatment more convenient. Oxidized coenzyme Q10 is more stable than reduced coenzyme Q10, and as compared with the coenzyme Q10 obtained by fermentative production in the prior art, high-content oxidized coenzyme Q10 degrades in a less amount in organisms. In addition, the fermentation method of the present application has a high potency.

13 Claims, 1 Drawing Sheet

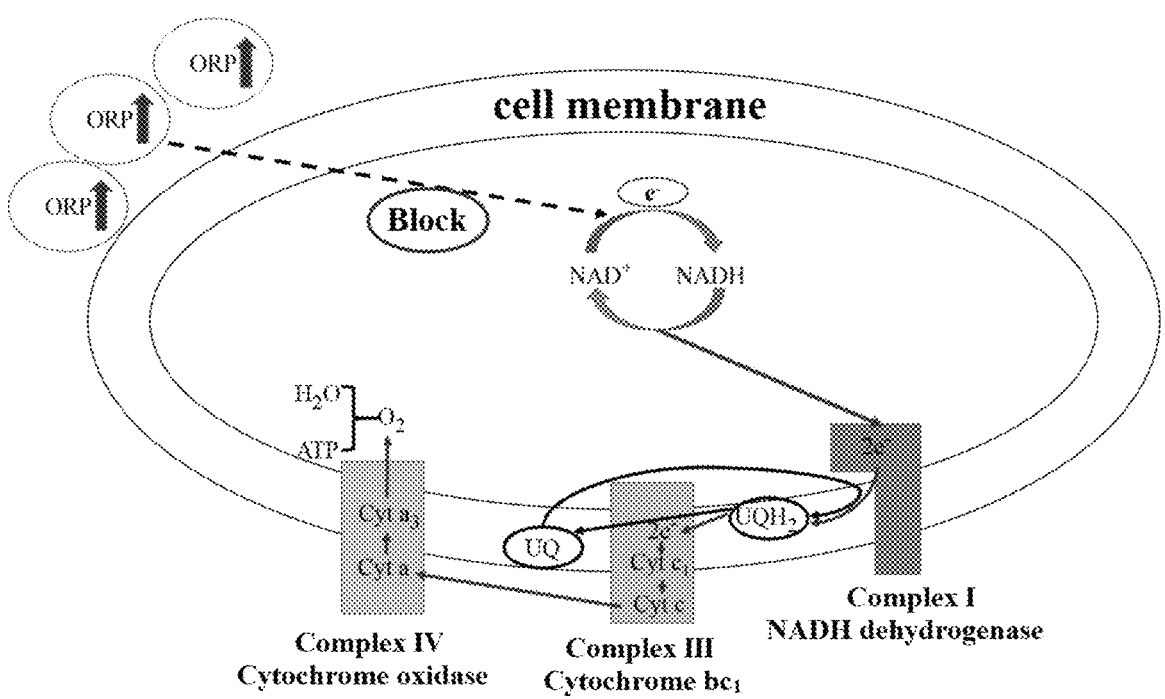

METHOD FOR FERMENTATIVE PRODUCTION OF OXIDIZED COENZYME Q10

TECHNICAL FIELD

The present application relates to the field of microbial fermentation, and in particular to a fermentation method which enables a production strain (e.g., *Rhodobacter sphaeroides*) to yield high-content (e.g., 70% or more, 80% or more, or 90% or more) oxidized coenzyme Q10 by regulating the ORP (Oxidation-Reduction Potential).

BACKGROUND

Coenzyme Q10 (CoQ10) is also known as ubiquinone or ubidecarenone, and its chemical name is 2,3-dimethoxy-5-methyl-6-decaprenyl benzoquinone. The biological activity of coenzyme Q10 comes from the oxidation-reduction properties of the quinone ring thereof and the physicochemical properties of the side chain thereof. Coenzyme Q10 is a natural antioxidant and cell metabolism activator produced by a cell per se, and it has functions such as anti-oxidation property, eliminating free radicals, improving immunity of the body, anti-aging, etc. Clinically, it is widely applied in the treatment of various diseases such as heart diseases, cancers, diabetes, acute and chronic hepatitis, and Parkinson's disease, and it also has broad applications in foods, cosmetics, and anti-aging health products.

At present, microbial fermentation is the major way to produce coenzyme Q10. The production of coenzyme Q10 by microbial fermentation has great competitive advantages in terms of both product quality and safety, and is suitable for large-scale industrial production.

The fermentation stage of microbiological production of coenzyme Q10 is generally divided into the following two stages: 1) a bacterial growth stage (also known as a microbial growth and reproduction stage), in which stage, it is generally necessary to maintain sufficient oxygen supply and nutrition so that microorganisms rapidly grow and reproduce to reach the bacterial concentration required for production, and meanwhile, the synthesis of the metabolite coenzyme Q10 starts quickly; 2) a coenzyme Q10 synthesis and accumulation stage (sometimes also referred to as a synthesis stage), at which stage, the fermentative bacteria rapidly consume oxygen, the dissolved oxygen in a fermentation broth is usually at a low level, and the fermentative microorganisms are in an oxygen-limited state, during which time the metabolite coenzyme Q10 is quickly synthesized and accumulated. The synthesis and accumulation stage is usually divided, based on the changes in the potency of coenzyme Q10 in the fermentation broth, into an early phase (the potency of coenzyme Q10 maintains a steep ascendant growth curve), a middle phase (the growth curve of the potency of coenzyme Q10 slows down, but the potency still maintains a significant growing trend) and a late phase (the growth curve of the potency of coenzyme Q10 tends to be steady, and the potency slightly increases along with the fermentation time). In general, the time interval between the early, the middle, and the late phases of the coenzyme Q10 synthesis and accumulation stage is about 10 to 20 hours.

As disclosed in CN102876743B, the fermentation process is regulated by a phased oxygen supply control strategy: a high oxygen supply is adopted in the bacterial growth stage and the early phase of the synthesis and accumulation stage of the fermentation process to promote rapid growth of the bacteria and quick start of coenzyme Q10 synthesis; after bacterial growth enters a stable phase (the bacteria no longer exhibit a significant net increase), the oxygen supply is reduced in phases to maintain a high coenzyme Q10 specific production rate and decrease the consumption of the substrate glucose. Such a phased change of oxygen supply mode may result in best physiological property status of the production bacteria and reduce the cost of coenzyme Q10 production.

In the process of producing coenzyme Q10 by microbial fermentation, those skilled in the art usually achieve the goal of high yields of coenzyme Q10 by adjusting influence factors such as the strain, the dissolved oxygen, the temperature, the pressure, the medium, and the nutrient feeding rate in the fermentation broth. For example, patent CN105420417A proposes that the fermentation process of coenzyme Q10 is controlled synergistically by adjusting the oxygen consumption rate (dissolved oxygen) and conductivity (nutrient feeding rate); while patent CN104561154A adjusts process parameters by using the shape of the bacteria in the fermentation process as a criterion; patent CN103509729B modifies *Rhodobacter sphaeroides* to improve its ability to synthesize coenzyme Q10. The common feature of these processes is that the produced coenzyme Q10 is a mixture of oxidized coenzyme Q10 and reduced coenzyme Q10, and the proportion of the reduced coenzyme Q10 is relatively high. In particular, in the process described in U.S. Pat. No. 7,910,340B2, after fermentation is completed, the content of reduced coenzyme Q10 in the coenzyme Q10 produced by microorganisms is 70% or more.

Since oxidized coenzyme Q10 and reduced coenzyme Q10 can be converted to each other in cells, either type of coenzyme Q10 can function as an electron transporter and perform relevant physiological functions. Moreover, because oxidized coenzyme Q10 is relatively stable and easier to preserve, there has been an increasing market demand for oxidized coenzyme Q10 in recent years.

None of the aforementioned patents CN105420417A, CN104561154A, CN103509729B reports any special treatment of the coenzyme Q10 produced by microorganisms to convert reduced coenzyme Q10 into oxidized coenzyme Q10. Although the U.S. Pat. No. 7,910,340B2 proposes that an oxidation means can be adopted in a post-treatment process to convert most of reduced coenzyme Q10 into oxidized coenzyme Q10, the post-treatment process is complicated and its cost is high. There is also no report in the prior art on a method for directly producing high-content oxidized coenzyme Q10 with microbial fermentation.

SUMMARY

Problems to be Solved by the Disclosure

The present disclosure aims to solve the problems such as low proportion of oxidized coenzyme Q10 and complicated post-treatment process of microbial fermentation methods in the prior art, and provides a method for fermentative production which enables a production strain (e.g., *Rhodobacter sphaeroides*) to yield high-content oxidized coenzyme Q10 by controlling the ORP of a fermentation broth.

Means for Solving the Problems

The present application relates to the following method for fermentative production of oxidized coenzyme Q10:

A method for fermentative production of oxidized coenzyme Q10, wherein in the fermentation process of a production strain, the oxidation-reduction potential (ORP) of a fermentation broth is controlled to be −50 to 300 mV, and preferably the oxidation-reduction potential (ORP) of the fermentation broth is controlled to be 50 to 200 mV.

In the above method for fermentative production, the oxidation-reduction potential (ORP) of the fermentation broth is controlled by at least one of the following means: adjusting the dissolved oxygen of the fermentation broth, and controlling the pH of the fermentation broth; preferably, the means of controlling the dissolved oxygen of the fermentation broth is combined with the means of controlling the pH of the fermentation broth.

In the above method for fermentative production, the dissolved oxygen in the fermentation broth is controlled by at least one of the following means: controlling the stirring input power per unit volume of a fermenter, controlling the air inlet flow per unit volume of the fermentation broth, and controlling the internal pressure of the fermenter; preferably, two or more of the above means are combined to control the dissolved oxygen in the fermentation broth.

In the above method for fermentative production, the stirring input power per unit volume of the fermenter is 0.25 to 0.50 kw/m$^3$, the air inlet flow per unit volume of the fermentation broth is 1.0 to 15.0 vvm, and/or the internal pressure of the fermenter is 0.05 to 0.3 MPa; preferably, the stirring input power per unit volume of the fermenter is 0.30 to 0.40 kw/m$^3$, the air inlet flow per unit volume of the fermentation broth is 5.0 to 8.0 vvm, and/or the internal pressure of the fermenter is 0.08 to 0.15 MPa.

In the above method for fermentative production, the pH of the fermentation broth is controlled by controlling the pH of the fermentation broth to be 3.5 to 6.0; preferably, the pH of the fermentation broth is controlled by controlling the pH of the fermentation broth to be 4.0 to 5.0; still preferably, the pH of the fermentation broth is controlled by means of adding an acid or adding a base; further preferably, the pH of the fermentation broth is controlled by means of adding the acid or the base in phases or continuously.

In the above method for fermentative production, the acid is an organic or an inorganic acid and/or the base is an organic base or an inorganic base; preferably, the acid is one or two or more of phosphoric acid, hydrochloric acid, sulfuric acid, lactic acid, propionic acid, citric acid, and oxalic acid, and/or preferably the base is one or two or more of ammonia water, sodium hydroxide, and liquid ammonia; and more preferably, the acid is phosphoric acid, lactic acid, or citric acid, and/or the base is ammonia water or liquid ammonia.

In the above method for fermentative production, the ORP of the fermentation broth is controlled in the coenzyme Q10 synthesis and accumulation stage in the fermentation process; preferably, the ORP of the fermentation broth is controlled in the middle or the late phase of the coenzyme Q10 synthesis and accumulation stage in the fermentation process; still preferably, the ORP of the fermentation broth is controlled in the late phase of the coenzyme Q10 synthesis and accumulation stage in the fermentation process.

In the above method for fermentative production, the conductivity of the fermentation broth is controlled to be 5.0 to 30.0 ms/cm in the fermentation process; preferably, in the bacterial growth stage, the oxygen consumption rate is controlled to be between 30 and 150 mmol/(L·h) and the conductivity of the fermentation broth is controlled to be between 5.0 and 30.0 ms/cm; still preferably, in the coenzyme Q10 synthesis and accumulation stage, the oxygen consumption rate is controlled to be between 60 and 120 mmol/(L·h), and the conductivity of the fermentation broth is controlled between 8.0 and 15.0 ms/cm.

In the above method for fermentative production, the production strain is *Rhodobacter sphaeroides*; preferably, the *Rhodobacter sphaeroides* is a naturally-selected strain, a strain selected by a physical or chemical mutagenesis method, or a strain modified by a genetic engineering method; more preferably, the *Rhodobacter sphaeroides* is a *Rhodobacter sphaeroides* strain of Deposit No. CGMCC No. 5997, a *Rhodobacter sphaeroides* strain of Deposit No. CGMCC No. 5998, or a *Rhodobacter sphaeroides* strain of Deposit No. CGMCC No. 5999.

In the above method for fermentative production, the coenzyme Q10 is high-content oxidized coenzyme Q10; and preferably the content of oxidized coenzyme Q10 in the high-content oxidized coenzyme Q10 is 96% or more, more preferably 97% or more, and most preferably 99% or more.

The present application also relates to coenzyme Q10 prepared by the above method, wherein the coenzyme Q10 is high-content oxidized coenzyme Q10; and preferably the content of oxidized coenzyme Q10 in the high-content oxidized coenzyme Q10 is 96% or more, more preferably 97% or more, and most preferably 99% or more.

The coenzyme Q10 prepared by the above method, wherein the coenzyme Q10 is used for preparing foods, functional nutritional foods, special healthy foods, nutritional supplements, nutrients, animal medicinal materials, beverages, feeds, cosmetics, medicines, medicaments, and preventive drugs.

Advantageous Effects

The present application provides a method for fermentative production of high-content oxidized coenzyme Q10, which has at least the following effects:

By controlling the oxidation-reduction potential (ORP) of the fermentation broth, the oxidized coenzyme Q10 content in the coenzyme Q10 produced by the microorganism can reach 96% or more, and the product is substantially composed of a single component, which makes post-treatment more convenient; oxidized coenzyme Q10 is more stable than reduced coenzyme Q10, and as compared with the coenzyme Q10 obtained by the fermentative production in the prior art, high-content oxidized coenzyme Q10 degrades in a less amount in organisms; in addition, the fermentation method of the present application has a high potency.

BRIEF DESCRIPTION OF THE DRAWINGS

FIG. 1 is a diagram showing the process of electron transfer in *Rhodobacter sphaeroides*.

DISCLOSURE DETAILED DESCRIPTION

The present application provides a method for fermentative production of high-content oxidized coenzyme Q10, which produces high-content oxidized coenzyme Q10 by controlling the oxidation-reduction potential (ORP) of a fermentation broth in the fermentation process. The ORP is controlled to be −50 to 300 mV, and preferably the ORP of the fermentation broth is controlled to be 50 to 200 mV.

The strain suitable for use in the method of the present disclosure is not particularly limited, and it may be an existing production strain for producing coenzyme Q10, or engineering bacteria modified by a conventional method or by applying a genetic engineering method.

Preferably, the strain for fermentative production of coenzyme Q10 is *Rhodobacter sphaeroides*. *Rhodobacter sphaeroides* is a photosynthetic bacterium belongs to the species *sphaeroides* of the genus *Rhodobacter*.

More preferably, the *Rhodobacter sphaeroides* is a naturally-selected strain, a strain selected by a physical or chemical mutagenesis method, or a strain modified by a genetic engineering method. Further preferably, the strain used for fermentative production of coenzyme Q10 is a *Rhodobacter sphaeroides* strain of Deposit No. CGMCC No. 5997, a *Rhodobacter sphaeroides* strain of Deposit No. CGMCC No. 5998, or a *Rhodobacter sphaeroides* strain of Deposit No. CGMCC No. 5999.

In the prior art, in the coenzyme Q10 synthesis and accumulation stage, the ORP of the fermentation broth is usually controlled to be between −150 and −300 mV so as to maintain a high yield of coenzyme Q10. And due to the physiological action of the bacteria per se, the produced coenzyme Q10 exists in a mixed form of oxidized type and reduced type, of which the reduced type comprises about 70%. The present application provides a method for enabling fermentative microorganisms to produce oxidized coenzyme Q10 by controlling the ORP of the fermentation broth. In the present application, the ORP is controlled to be −50 to 300 mV, and the percentage of the oxidized coenzyme Q10 produced by the fermentative bacteria reaches 96% or more. The mechanism of the method is shown in FIG. 1. There is a cycle of $NAD^+ \rightleftharpoons NADH$ in *Rhodobacter sphaeroides* to carry out electron transfer, which provides energy for the metabolism of *Rhodobacter sphaeroides*. Wherein the reducing power provided by the NADH in a reduction state is one of the necessary conditions for the conversion of oxidized coenzyme Q10 into reduced coenzyme Q10 in cells. The environment of the fermentation broth will greatly affect the cycle of $NAD^+ \rightleftharpoons NADH$ in cells, wherein the oxidation-reduction potential (ORP) of the fermentation broth is the key indicator. Under normal circumstances, the ORP value of the fermentation broth is in the range of −150 to −300 my. That is, when the fermentation broth is under reducing conditions, most of the coenzyme Q10 produced by *Rhodobacter sphaeroides* is reduced coenzyme Q10. By increasing the ORP in the fermentation broth, oxidizability in the fermentation broth environment is enhanced, which results in the inhibition of the conversion from NAD+ to NADH, and in the absence of adequate reducing power provided by NADH, for the coenzyme Q10 produced by *Rhodobacter sphaeroides*, the conversion from oxidized coenzyme Q10 into reduced coenzyme Q10 is also greatly affected, which ultimately is manifested in generation of a large amount of oxidized coenzyme Q10 in cells.

The above-mentioned method for fermentative production of high-content oxidized coenzyme Q10 is suitable for use in the whole process of microbial fermentation. Preferably, the above method is used in the coenzyme Q10 synthesis and accumulation stage. Further, the ORP of the fermentation broth is controlled in the middle or the late phase of the coenzyme Q10 synthesis and accumulation stage in the fermentation process. More preferably, the ORP of the fermentation broth is controlled in the late phase of the coenzyme Q10 synthesis and accumulation stage in the fermentation process.

In the above method, in the fermentation process, the ORP value of the fermentation broth is controlled by controlling the dissolved oxygen or the pH of the fermentation broth, or by synergistically controlling the dissolved oxygen and the pH of the fermentation broth. As a preferred embodiment, the ORP value of the fermentation broth is controlled by synergistically controlling the dissolved oxygen and the pH of the fermentation broth.

The change in dissolved oxygen concentration in the fermentation process is a dynamic balance between oxygen supply rate and oxygen consumption rate. In the present application, the oxygen supply in the fermentation broth is increased by means of controlling the stirring input power per unit volume of the fermenter, controlling the air inlet flow per unit volume of the fermentation broth, controlling the internal pressure of the fermenter, or random combinations of the three means, so as to increase the dissolved oxygen in the fermentation broth and enable the ORP value of the fermentation broth to reach −50 to 300 mv. Wherein it is preferable to control the stirring input power per unit volume of the fermenter to be 0.25 to 0.50 kw/m$^3$, to control the air inlet flow per unit volume of the fermentation broth to be 1.0 to 15.0 vvm (wherein vvm refers to air volume/culture volume/min; i.e., the ratio of the ventilation volume per minute to the actual volume of the fermentation broth in the fermenter), and to control the internal pressure of the fermenter to be 0.05 to 0.3 MPa; and it is more preferable to control the stirring input power per unit volume of the fermenter to be 0.30 to 0.40 kw/m$^3$, to control the air inlet flow per unit volume of the fermentation broth to be 5.0 to 8.0 vvm, and to control the internal pressure of the fermenter to be 0.08 to 0.15 MPa.

In the present application, it is also preferable to control the pH of the fermentation broth to enable the ORP value of the fermentation broth to reach −50 to 300 mv. For example, the pH may be controlled to be 3.5 to 6.0, and more preferably, the pH may be controlled to be 4.0 to 5.0. And the control is preferably performed by adding an acid or a base. The acid may be a conventional acid that is conventionally used to adjust the pH of a fermentation broth, and is preferably one or two or more of phosphoric acid, hydrochloric acid, sulfuric acid, lactic acid, propionic acid, citric acid, and oxalic acid; the base may be a conventional base that is conventionally used to adjust the pH of a fermentation broth, and is preferably one or two or more of ammonia water, sodium hydroxide, and liquid ammonia. As a preferred embodiment, the acid is phosphoric acid, lactic acid, or citric acid, and the base is ammonia water or liquid ammonia. In order to avoid drastic effects on the fermentative bacteria, the pH of the fermentation broth can be controlled by adding an acid or a base in phases or continuously.

In the above method, the conductivity of the fermentation broth is controlled to be 5.0 to 30.0 ms/cm to maintain the nutrient supply for the fermentative bacteria. Wherein, the conductivity of the fermentation broth is controlled by a feeding medium. The medium used in the present disclosure is not particularly limited, and it may be any conventional medium containing a carbon source, a nitrogen source, a phosphorus source, and micronutrients. For example, the feeding medium has the following formula: 8 to 12 g of yeast powder, 5 to 10 g of ammonium sulfate, 1 to 2 g of magnesium sulfate, 3 to 6 g of sodium chloride, 2 to 4 g of potassium dihydrogen phosphate, 2 to 4 g dipotassium hydrogen phosphate, 1 to 2 g of calcium chloride, and 0.013 to 0.025 g of biotin are contained per liter of the feed solution; and the pH is 7.0.

In the above-described fermentation method, there is no particular limitation on the temperature during fermentation, as long as the effects of the present application are not affected. From the viewpoint that the production strain can produce more oxidized coenzyme Q10, the temperature is preferably controlled to be 25 to 35° C.

In the present application, in a seed culture stage before the fermentative production of coenzyme Q10, culture can be performed using a conventional method in the art, and reference to a preferred culture means can be found in patent CN105483171A. Specifically, a medium having a $Fe^{2+}$ concentration of 0.1 to 0.5 mol/L is used in the seed culture stage, and the *Rhodobacter sphaeroides* strains are subjected to recovery and expansion with a seed medium sequentially, and then are screened to give fermentation seeds. The formula of the seed medium used in the method of the present disclosure is not particularly limited and may be any conventional medium containing a carbon source, a nitrogen source, a phosphorus source, and micronutrients. For example, the seed medium has the following formula as disclosed in CN105483171A: in addition to 0.1 to 0.5 mol of $Fe^{2+}$, 1 g of yeast powder, 1 g of ammonium chloride, 1 g of sodium chloride, 0.0028 g of ferric citrate, 0.6 g of potassium dihydrogen phosphate, 0.9 g of dipotassium hydrogen phosphate, 0.25 g of magnesium sulfate, 0.1 g of calcium chloride are contained per liter of the medium; and the pH is adjusted to 7.0.

In the present application, during the fermentation process, in the bacterial growth stage of *Rhodobacter sphaeroides* and preferably also the early and/or the middle phases of the coenzyme Q10 synthesis and accumulation stage, there may be carried out the action of combining conventional means in the art with the technical solutions of the present application, and preferably, with reference to patent CN105420417A, be carried out the action of combining the use of on-line control of oxygen consumption rate and conductivity with the technical solutions of the present application. Wherein, the oxygen consumption rate is adjusted by the stirring speed and the air flow, and the conductivity is adjusted by means of continuous feeding or batch feeding. Specifically, the oxygen consumption rate is controlled to be between 30 and 150 mmol/(L·h) during the bacterial growth stage of *Rhodobacter sphaeroides*, and the conductivity is stabilized between 5.0 and 30.0 ms/cm; in the coenzyme Q10 synthesis and accumulation stage, the oxygen consumption rate is controlled between 60 and 120 mmol/(L·h), while the conductivity is stabilized between 8.0 and 15.0 ms/cm. In the fermentation stage, the medium used is a conventional medium in the art which contains a carbon source, a nitrogen source, a phosphorus source, and micronutrients. For example, 8 g of yeast powder, 3 g of ammonium chloride, 2.8 g of sodium chloride, 0.005 g of ferric citrate, 0.6 g of potassium dihydrogen phosphate, 0.9 g of dipotassium hydrogen phosphate, 12.55 g of magnesium sulfate, 0.1 g of calcium chloride are contained per liter of the medium; and the pH is 7.0.

Examples of *Rhodobacter sphaeroides*

Deposit No.: CGMCC No. 5997, CGMCC No. 5998, and CGMCC No. 5999; Depositary Institution: China General Microbiological Culture Collection Center; Address of Depositary Institution: Institute of Microbiology, Chinese Academy of Sciences, No. 3, Yard No. 1, West Beichen Road, Chaoyang District, Beijing; Date of Deposit: Apr. 13, 2012; Patent Document where the strains are disclosed: CN105420417 (A); Publication Date: Mar. 23, 2016.

In addition, the above three strains are also disclosed in CN105483171A (Apr. 13, 2016); CGMCC No. 5998 is also disclosed in CN103509729 A (Jan. 15, 2014).

The present disclosure will be further described with reference to specific Examples. However, the present disclosure is not limited to the Examples described below.

EXAMPLES

Strain and Pre-fermentation Culture

Strain: *Rhodobacter sphaeroides*, a strain of Deposit No. CGMCC No. 5997, CGMCC No. 5998, or CGMCC No. 5999.

Pre-fermentation culture: a cultured slant was washed with sterile water to form a bacterial suspension with a concentration of $10^8$ to $10^9$ cells per milliliter; 2 ml of the prepared bacterial suspension was inoculated into a medium in a mother flask for seed culture, wherein the medium was 100 ml, and the culture was performed for 28 to 30 hours at 32° C., with a rotation rate of 180 rpm.

Seed medium (g/L): 1 g of yeast powder, 1 g of $NH_4Cl$, 1 g of sodium chloride, 2.8 mg of ferric citrate, 0.6 g of $KH_2PO_4$, 0.9 g of $K_2HPO_4$, 0.25 g of $MgSO_4$, 0.1 g of $CaCl_2$, 0.5 µg of biotin; and the pH was 7.0.

The inoculum amount of inoculating the *Rhodobacter sphaeroides* strain obtained through the above seed culture into the fermenter may be a conventional amount in the art, such as 10 to 300 ml, preferably 25 to 200 ml, and further preferably 50 to 100 ml. The inoculum amount can be adjusted as needed.

Determination of the potency: sample preparation: under nitrogen atmosphere, 1 ml of the fermentation broth was taken and put into a 10 ml centrifuge tube, and 180 µl of 1 mol/l HCl was added, mixed well, and allowed to stand for 3 to 5 min, and then the mixture was placed in a 92° C. water bath to heat for 30 min; supernatant was removed by centrifugation, and 8 ml of leaching liquor (ethyl acetate:ethanol=5:3) was added into the mixture to perform leaching for 2 h; and the mixture was subjected to an HPLC reverse phase test. HPLC conditions: C18 column: 150 mm*4.6 mm, mobile phase was methanol:isopropanol=75:25 (by volume), flow: 1.00 ml/min, detection wavelength: 275 nm, and injection volume: 40 µl. Retention time: 12 min.

Determination of the content of oxidized coenzyme Q10: sample preparation: under nitrogen atmosphere, 1 ml of the fermentation broth was taken and put into a 10 ml centrifuge tube, and 180 µl of 1 mol/l HCl was added, mixed well, and allowed to stand for 3 to 5 min, and then the mixture was placed in a 92° C. water bath to heat for 30 min; supernatant was removed by centrifugation, and 8 ml of leaching liquor (ethyl acetate:ethanol=5:3) was added to the solution to perform leaching for 2 h; and the solution was subjected to an HPLC reverse phase test. HPLC conditions: column: YMC-Pack, 4.6 mm* 250 mm, mobile phase was methanol:n-hexane=85:15 (by volume), flow: 1 mL/min, detection wavelength: 275 nm, and injection volume: 40 µl. Retention time: for reduced coenzyme Q10 was 13.5 min and for oxidized coenzyme Q10 was 22.0 min.

Example 1

At 30° C., 50 ml of the *Rhodobacter sphaeroides* strain CGMCC No. 5998 obtained from the seed culture was inoculated into a 5 L fermenter containing a fermentation medium to start fermentation. The oxygen supply conditions for the fermenter are controlled as follows: the air inlet flow per unit volume of the fermentation broth was controlled to be 1.0 vvm, the stirring input power per unit volume of the fermenter was controlled to be 0.25 kw/m³, and the internal pressure of the fermenter was controlled to be 0.1 MPa. And the pH of the fermentation broth was controlled to be about 7.0 by continuous feeding of liquid ammonia.

Fermentation medium was: 8 g of yeast powder, 3 g of ammonium chloride, 2.8 g of sodium chloride, 0.005 g of ferric citrate, 0.6 g of potassium dihydrogen phosphate, 0.9 g of dipotassium hydrogen phosphate, 12.55 g of magnesium sulfate, and 0.1 g of calcium chloride were contained per liter of the medium; the pH was adjusted to 7.0.

The conductivity throughout the fermentation process was controlled to be about 12 ms/cm by a feeding medium. The feeding medium contained 8 g of yeast powder, 5 g of ammonium sulfate, 1 g of magnesium sulfate, 3 g of sodium chloride, 2 g of potassium dihydrogen phosphate, 2 g of dipotassium hydrogen phosphate, 1 g of calcium chloride, and 0.013 g of biotin per liter of the feed solution; and the pH value was adjusted to 7.0.

After continuous fermentation for 15 hours, the ORP value of the fermentation broth as measured was −35 mv. A portion of the fermentation broth was taken, subjected to extraction under an inert gas atmosphere, and subjected to tests (with reference to the determination of potency and the determination of content as described above). The content ratio of oxidized coenzyme Q10 to reduced coenzyme Q10 in the cells was 96.5:3.5.

Throughout this Example, a high oxygen supply was maintained, as well as a high stirring input power and a high pressure in the fermenter, so that a relatively high concentration of the dissolved oxygen in the fermentation broth was sustained, the ORP value of the fermentation broth was always −35 mv or more, and the microorganism in the fermentation broth had been under growing and reproducing status. According to the test results, it can be confirmed that when the ORP value of the fermentation broth is maintained at a certain value or more, the fermentative microorganisms at the bacterial growth stage produces high-content oxidized coenzyme Q10.

Example 2

At 30° C., 40 ml of the *Rhodobacter sphaeroides* strain CGMCC No. 5999 obtained from the seed culture was inoculated into a 5 L fermenter containing a fermentation medium to start fermentation (the air inlet flow per unit volume of the fermentation broth in the fermenter was controlled to be 0.45 vvm, the stirring input power per unit volume of the fermenter was controlled to be 0.1 kw/m$^3$, and the pressure of the fermenter was 0.02 MPa). The conductivity of the fermentation broth was 12 ms/cm, and the pH value was controlled to be about 7.0.

Fermentation medium was: 8 g of yeast powder, 3 g of ammonium chloride, 2.8 g of sodium chloride, 0.005 g of ferric citrate, 0.6 g of potassium dihydrogen phosphate, 0.9 g of dipotassium hydrogen phosphate, 12.55 g of magnesium sulfate, and 0.1 g of calcium chloride were contained per liter of the medium; the pH value was adjusted to 7.0.

Feeding medium: 10 g of yeast powder, 8 g of ammonium sulfate, 1.5 g of magnesium sulfate, 5 g of sodium chloride, 3 g of potassium dihydrogen phosphate, 3 g of dipotassium hydrogen phosphate, 1 g of calcium chloride, and 0.020 g of biotin were contained per liter of the feed solution; the pH value was adjusted to 7.0.

After the dissolved oxygen as measured in the fermentation broth no longer declined, a certain amount of phosphoric acid was slowly and continuously fed into the fermentation broth to adjust the pH of the fermentation broth to about 4.0 within one hour. Liquid ammonia was continuously fed to keep the pH stable at about 4.0. The air inlet flow per unit volume of the fermentation broth in the fermenter, the stirring input power per unit volume of the fermenter, and the pressure of the fermenter remained the same. And the conductivity of the fermentation broth was 12 ms/cm. After the pH was stabilized, the ORP value of the fermentation broth as measured was between 58 and 135mv.

10 hours later, a portion of the fermentation broth was taken, subjected to extraction under an inert gas atmosphere, and subjected to tests. The content ratio of oxidized coenzyme Q10 to reduced coenzyme Q10 in the cells was 97.3:2.7.

In this Example, after the dissolved oxygen in the fermentation broth no longer decreased, the fermentation process entered the coenzyme Q10 synthesis and accumulation stage. The pH value was adjusted in the early phase of the coenzyme Q10 synthesis and accumulation stage. The final test results demonstrate that controlling the ORP value by adjusting the pH value enables the fermentative microorganism to effectively produce high-content oxidized coenzyme Q10 in the early phase of the coenzyme Q10 synthesis and accumulation stage.

Example 3

At 30° C., 90 ml of the *Rhodobacter sphaeroides* strain CGMCC No. 5997 obtained from the seed culture was inoculated into a 10 L fermenter containing a fermentation medium to start fermentation (the air inlet flow per unit volume of the fermentation broth in the fermenter was controlled to be 0.6 vvm, the stirring input power per unit volume of the fermenter was controlled to be 0.1 kw/m$^3$, and the pressure of the fermenter was 0.02 MPa). The conductivity of the fermentation broth was 12 ms/cm, and the pH value was controlled to be about 7.0.

Fermentation medium was: 8 g of yeast powder, 3 g of ammonium chloride, 2.8 g of sodium chloride, 0.005 g of ferric citrate, 0.6 g of potassium dihydrogen phosphate, 0.9 g of dipotassium hydrogen phosphate, 12.55 g of magnesium sulfate, and 0.1 g of calcium chloride were contained per liter of the medium; the pH was adjusted to 7.0.

Feeding medium was: 12 g of yeast powder, 10 g of ammonium sulfate, 2 g of magnesium sulfate, 6 g of sodium chloride, 4 g of potassium dihydrogen phosphate, 4 g of dipotassium hydrogen phosphate, 2 g of calcium chloride, and 0.025 g of biotin were contained per liter of the feed solution; the pH value was adjusted to 7.0.

After the dissolved oxygen as measured in the fermentation broth no longer declined, a certain amount of phosphoric acid was slowly and continuously fed into the fermentation broth to adjust the pH of the fermentation broth to about 5.0 within one hour. Liquid ammonia was continuously fed to maintain the pH at about 5.0. Meanwhile, the air inlet flow per unit volume of the fermentation broth in the fermenter was controlled to be 5.0 vvm, the stirring input power per unit volume of the fermenter was controlled to be 0.3 kw/m$^3$, and the pressure of the fermenter was 0.08 MPa. After stabilization, the ORP value of the fermentation broth was maintained between 100 and 210 mV.

10 hours later, a portion of the fermentation broth was taken, subjected to extraction under an inert gas atmosphere, and subjected to tests. The content ratio of oxidized coenzyme Q10 to reduced coenzyme Q10 in the cells was 99.1:0.9.

In this Example, the ORP value of the fermentation broth was controlled by synergistically controlling the oxygen supply conditions of the fermentation broth and the pH value of the fermentation broth. Similarly, in the Example, the adjustment was performed in the coenzyme Q10 synthesis and accumulation stage in the fermentation process, and the ratio of the yielded oxidized coenzyme Q10 reached 99.1%.

Example 4

1) At 30° C., 120 ml of the *Rhodobacter sphaeroides* strain CGMCC No. 5999 obtained from the seed culture was inoculated into a 10 L fermenter containing a fermentation medium to start fermentation (the air inlet flow per unit volume of the fermentation broth in the fermenter was controlled to be 0.4 vvm, the stirring input power per unit volume of the fermenter was controlled to be 0.1 kw/m$^3$, and the pressure of the fermenter was 0.02 MPa). The oxygen consumption rate was controlled to be 50 mmol/(L·h), the conductivity of the fermentation broth was 12 ms/cm, and the pH value was controlled to be about 7.0.

Fermentation medium was: 8 g of yeast powder, 3 g of ammonium chloride, 2.8 g of sodium chloride, 0.005 g of ferric citrate, 0.6 g of potassium dihydrogen phosphate, 0.9 g of dipotassium hydrogen phosphate, 12.55 g of magnesium sulfate, and 0.1 g of calcium chloride were contained per liter of the medium; the pH value was adjusted to 7.0.

Feeding medium was: 12 g of yeast powder, 10 g of ammonium sulfate, 2 g of magnesium sulfate, 6 g of sodium chloride, 4 g of potassium dihydrogen phosphate, 4 g of dipotassium hydrogen phosphate, 2 g of calcium chloride, and 0.025 g of biotin were contained per liter of the feed solution; the pH value was adjusted to 7.0.

2) 15 hours later, the oxygen supply was increased (the air inlet flow per unit volume of the fermentation broth in the fermenter was controlled to be 0.6 vvm, the stirring input power per unit volume of the fermenter was controlled to be 0.2 kw/m$^3$, and the pressure of the fermenter was 0.04 MPa). The oxygen consumption rate was raised to 70 mmol/(L·h) and then remained stable, the conductivity of the fermentation broth was 12 ms/cm, and the pH value was controlled at 7.0. The fermentation continued. At this time, the fermentation was in the bacterial growth stage.

3) 20 hours later, the oxygen supply was increased again (the air inlet flow per unit volume of the fermentation broth in the fermenter was controlled to be 0.8 vvm, the stirring input power per unit volume of the fermenter was controlled to be 0.2 kw/m$^3$, and the pressure of the fermenter was 0.05 MPa). The oxygen consumption rate was raised to 90 mmol/(L·h) and then remained stable, the conductivity of the fermentation broth was 12 ms/cm, and the pH value was controlled at 7.0. The fermentation continued. At this time, the fermentation was in the bacterial growth stage.

4) 10 hours later, the oxygen consumption rate was maintained at about 70 mmol/(L·h), the conductivity of the fermentation broth was controlled at 12 ms/cm, and the pH value was controlled to be about 6.0. The fermentation continued. At this time, the fermentation was in the early phase of the coenzyme Q10 synthesis and accumulation stage.

5) 20 hours later, the increase of the fermentation potency tended to be steady at this time, and the fermentation entered the late phase of the coenzyme Q10 synthesis and accumulation stage. The air inlet flow per unit volume of the fermentation broth in the fermenter was controlled to be 6.0 vvm, the stirring input power per unit volume of the fermenter was controlled to be 0.2 kw/m$^3$, and the pressure of the fermenter was 0.1 MPa. By continuously adding phosphoric acid, the pH value was adjusted to about 3.5 in about 2 h. The conductivity of the fermentation broth was controlled at 12 ms/cm. The fermentation continued. After stabilization, the ORP value of the fermentation broth was maintained between 100 and 200 mv.

6) 15 hours later, the fermentation was stopped. A portion of the fermentation broth was taken, subjected to extraction under an inert gas atmosphere, and subjected to tests. The potency was 3182 mg/L, and oxidized coenzyme Q10: reduced coenzyme Q10 was 99.3:0.7.

In this Example, the ORP value of the fermentation broth was controlled in the late phase of the coenzyme Q10 synthesis and accumulation stage in the fermentation process. While high-content oxidized coenzyme Q10 was efficiently produced, a gratifying increase of the potency of the fermentative microorganism was also achieved.

APPLICABILITY

By controlling the oxidation-reduction potential (ORP) of the fermentation broth, the method for fermentative production of oxidized coenzyme Q10 of the present application enables the oxidized coenzyme Q10 content in the coenzyme Q10 produced by the microorganisms to reach 96% or more, which makes post-treatment convenient.

The produced high-content oxidized coenzyme Q10 is more stable than reduced coenzyme Q10, and can be used for preparing foods, functional nutritional foods, special healthy foods, nutritional supplements, nutrients, animal medicinal materials, beverages, feeds, cosmetics, medicines, medicaments, and preventive drugs.

What is claimed is:

1. A method for fermentative production of oxidized coenzyme Q10 in a fermenter, which comprises:
    controlling the oxidation-reduction potential (ORP) of a fermentation broth containing a member selected from the group consisting of Rhodobacter sphaeroides strain of Deposit No. CGMCC No. 5997, Rhodobacter sphaeroides strain of Deposit No. CGMCC No. 5998, or *Rhodobacter sphaeroides* strain of Deposit No. CGMCC No. 5999 to be between −50 to −300 mV by at least one of controlling the stirring input power per unit volume of the fermenter to be between 0.25 and 0.50 kw/m$^3$, controlling the air inlet flow per unit volume of the fermentation broth in the fermenter to be between 1.0 and 15.0 vvm and controlling the internal pressure of the fermenter to be between 0.05 and 0.3 MPa, and
    maintaining the conductivity of the fermentation broth between 5.0 and 30.0 ms/cm by adding to the broth a feed solution having a pH of 7.0 and containing 0.013 to 0.025 grams of biotin per liter of feed solution.

2. The method for fermentative production according to claim 1 wherein the oxidation-reduction potential (ORP) of the fermentation broth is controlled by at least one of the following means: adjusting the dissolved oxygen of said fermentation broth, and controlling the pH of said fermentation broth.

3. The method for fermentative production according to claim 2, wherein the pH of said fermentation broth is controlled by controlling the pH of said fermentation broth to be 3.5 to 6.0.

4. The method for fermentative production according to claim 1, wherein the ORP of the fermentation broth is controlled in a coenzyme Q10 synthesis and accumulation stage in the fermentation process.

5. The method for fermentative production according to claim 1, wherein said coenzyme Q10 is high-content oxidized coenzyme Q10.

6. The method for fermentative production according to claim 1, wherein in a fermentation process of a production strain, the oxidation-reduction potential (ORP) of a fermentation broth is controlled to be 50 to 200 mV.

7. The method for fermentative production according to claim 1, wherein said stirring input power per unit volume of the fermenter is 0.30 to 0.40 kw/m$^3$, said air inlet flow per unit volume of the fermentation broth is 5.0 to 8.0 vvm, and/or said internal pressure of the fermenter is 0.08 to 0.15 MPa.

8. The method for fermentative production according to claim 3, wherein the pH of said fermentation broth is controlled by controlling the pH of said fermentation broth to be 4.0 to 5.0.

9. The method for fermentative production according to claim 3, wherein the pH of said fermentation broth is controlled by means of adding an acid or a base in phases or continuously.

10. The method for fermentative production according to claim 9, wherein said acid is one or two or more of phosphoric acid, hydrochloric acid, sulfuric acid, lactic acid, propionic acid, citric acid, and oxalic acid, and/or said base is one or two or more of ammonia water, sodium hydroxide, and liquid ammonia.

11. The method for fermentative production according to claim 10, wherein said acid is phosphoric acid, lactic acid, or citric acid, and/or said base is ammonia water or liquid ammonia.

12. The method for fermentative production according to claim 4, wherein the ORP of the fermentation broth is controlled in a middle or a late phase of the coenzyme Q10 synthesis and accumulation stage in the fermentation process.

13. The method for fermentative production according to claim 1, wherein in a bacterial growth stage, the oxygen consumption rate is controlled to be between 30 and 150 mmol/(L·h) and the conductivity of said fermentation broth is controlled to be between 5.0 and 30.0 ms/cm, and/or, in a coenzyme Q10 synthesis and accumulation stage, the oxygen consumption rate is controlled to be between 60 and 120 mmol/(L·h), and the conductivity of said fermentation broth is controlled between 8.0 and 15.0 ms/cm.

* * * * *

UNITED STATES PATENT AND TRADEMARK OFFICE
CERTIFICATE OF CORRECTION

PATENT NO. : 10,774,350 B2
APPLICATION NO. : 16/016813
DATED : September 15, 2020
INVENTOR(S) : Shenfeng Yuan et al.

Page 1 of 1

It is certified that error appears in the above-identified patent and that said Letters Patent is hereby corrected as shown below:

In the Claims

Column 12, Line 39, Claim 1, delete "-300" and insert -- 300 --.

Signed and Sealed this
Eighteenth Day of May, 2021

Drew Hirshfeld
*Performing the Functions and Duties of the*
*Under Secretary of Commerce for Intellectual Property and*
*Director of the United States Patent and Trademark Office*